United States Patent
Johnsen et al.

(10) Patent No.: US 9,982,033 B2
(45) Date of Patent: May 29, 2018

(54) FACTOR VIII POLYPEPTIDE TITERS IN CELL CULTURES

(75) Inventors: Laust Bruun Johnsen, Skodsborg (DK); Ida Hilden, Vanlose (DK); Gert Bolt, Vaerlose (DK); Thomas Dock Steenstrup, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 211 days.

(21) Appl. No.: 12/597,118

(22) PCT Filed: Apr. 30, 2008

(86) PCT No.: PCT/EP2008/055349
§ 371 (c)(1),
(2), (4) Date: Dec. 21, 2009

(87) PCT Pub. No.: WO2008/135501
PCT Pub. Date: Nov. 13, 2008

(65) Prior Publication Data
US 2010/0120094 A1   May 13, 2010

Related U.S. Application Data

(60) Provisional application No. 60/928,302, filed on May 9, 2007.

(30) Foreign Application Priority Data

May 4, 2007 (EP) ..................................... 07107477

(51) Int. Cl.
*C07K 14/755* (2006.01)
(52) U.S. Cl.
CPC .................. *C07K 14/755* (2013.01)
(58) Field of Classification Search
None
See application file for complete search history.

(56) References Cited

U.S. PATENT DOCUMENTS

| | | | |
|---|---|---|---|
| 5,250,421 A * | 10/1993 | Kaufman et al. | 435/69.6 |
| 5,672,502 A | 9/1997 | Birch et al. | |
| 5,679,549 A | 10/1997 | Chan | |
| 6,338,964 B1 | 1/2002 | Matanguihan et al. | |
| 7,122,634 B2 | 10/2006 | Lollar | |
| 2003/0203448 A1 * | 10/2003 | Reiter et al. | 435/69.1 |
| 2005/0227913 A1 | 10/2005 | Balasubramanian et al. | |

FOREIGN PATENT DOCUMENTS

| | | |
|---|---|---|
| EP | 254076 | 5/1991 |
| EP | 745672 | 11/2005 |
| EP | 1707634 | 10/2006 |
| JP | 1997-98796 | 4/1997 |
| JP | H0998796 | 4/1997 |
| JP | 2003-510070 A | 3/2003 |
| RU | 2285724 C2 | 10/2006 |
| WO | 87/04187 A1 | 7/1987 |
| WO | 88/08035 A1 | 10/1988 |
| WO | 90/02175 A1 | 3/1990 |
| WO | 97/43436 A1 | 11/1997 |
| WO | 2004/071420 A2 | 8/2004 |
| WO | 2006/103258 A1 | 10/2006 |

OTHER PUBLICATIONS

Foster, P.A., et al. 1990 Blood 75(10): 1999-2004.*
Ramani et al., "Lipid Bining Region (2303-2332) Is Involved in Aggregation of Recombinant Human FVIII (RFVIII)," J Pharm Sci (2005), vol. 94, No. 6, pp. 1288-1299.
Gilbert et al., "Specific Membrane Binding of Factor VIII Is Mediated by O-Phospho-L-Serine, Moiety of Phosphatidylserine," Bio Chem (1993), vol. 32, No. 37, pp. 9577-9585.
Purohit et al, The Journal of Biological Chemistry, "Lower Inhibitor Development in Hemophilia A Mice Following Administration of Recombinant Factor VIII-O-Phospho-L-Serine Complex", 2006, vol. 280, No. 18, pp. 17593-17600.
Hansen et al., "Proteolytic cleavage of recombinant two-chain factor VIII during cell culture production is mediated by protease(s) from lysed cells," Cytotechnology, 1997, vol. 24, No. 3, pp. 227-234.
Tanaka H, et al., Incongruent dissolution of hydroxyapatite in the presence of. phosphoserine, Journal :Colloid & Polymer Science, Year 1991, vol. 269, pp. 161-165.
Gomperts E. et al. "The Manufacturing Process of Recombinant Factor VIII, Recornbinate." Transfusion Medicine Reviews, vol. VI(4). pp. 247-251. (1992).
Ham, R.G. et al. "An Improved Nutrient Solution for Diploid Chinese Hamster and Human Cell Lines." Experimental Cell Research. vol. 29. pp. 515-526. (1963).
Kaufman et al. "Effect of von Williebrand Factor Coexpression on the Synthesis and Secretion of Factor VIII in Chineses Hamster Ovary Cells." Molecular and Cellular Biology. vol. 9(3). pp. 1233-1242. (1989).
Kyu Oh, H et al. "Purification of Recombinant Human B-Domain-Deleted Factor VII Using Anti-Factor VIII Monoclonal Antibody Selected by the Surface Plasmon Resonance Biosensor." Biotechnol. Prog. vol. 17. pp. 1119-1127. (2001).
Pittman et al. "Post-translational Requirements for Functional Factor V and Factor VIII Secretion in Mammalian Cells." The Journal of Biological Chemistry. vol. 269. pp. 17329-17337. (1994).
Terraube V. et al. "Factor VIII and von Willebrand factor interaction: biological, clinical and therapeutic importance." Haemophila. vol. 16. pp. 3-13. (2010).
Turecek P. et al. "Structure and Function of Recombinant von Willebrand Factor Drug Candidate." Seminars in Thrombosis and Hemostasis. vol. 36(5). pp. 510-521 (2010).

(Continued)

*Primary Examiner* — Marsha Tsay
(74) *Attorney, Agent, or Firm* — Rosemarie R. Wilk-Orescan

(57) ABSTRACT

The invention relates to a method for the production of a Factor VIII polypeptide, the method comprising the steps of a) culturing a mammalian cell expressing a Factor VIII polypeptide under conditions for expression of said Factor VIII polypeptide, said culturing conditions involving a cell culture medium comprising a C2-domain ligand, and b) isolating the expressed Factor VIII polypeptide from the mammalian cell by suitable means.

22 Claims, 4 Drawing Sheets

(56) References Cited

OTHER PUBLICATIONS

Mann KG et al., "The Molecular Biology of Blood Coagulation," Current Hematology, 1983, pp. 347-374.
Fang Hong et al., "The protein Structure and effect of factor VIII," Thrombosis Research, 2007, vol. 119, pp. 1-13.
Zachowski A, Phospholipids in animal eukaryotic membranes: transverse asymmetry and movement, Journal: Biochem. Journal, Year 1993, vol. 294, pp. 1-14.
Witting et al.Phagocytic Clearance of Apoptotic Neurons by Microglia/Brain Macrophages in Vitro: Involvement of Lectin-, Integrin-, and Phosphatidylserine-Mediated Recognition, Journal: Journal of Neurochemistry, Year 2000, vol. 75, No. 3, pp. 1060-1070.
Pratt Kathleen P et al: "Structure of the C2 domain of human factor VIII at 1.5 ANG resolution", Nature (London), Year 1999 vol. 402, No. 6760, pp. 439-442.
Spiegel Paul Clint Jr et al Structure of a factor VIII C2 domain-immunoglobulin G4kappa Fab complex: Identification of an inhibitory antibody epitope on the surface of factor VIII, Blood, Year 2001, vol. 98, No. 1, pp. 13-19.
DMEM/F12 medium composition; retrieved from the internet Jun. 18, 2013.
Table 3 of the patent updated to show cell viability data; submitted Jun. 17, 2015.
Ishaque et al., Cell Surface Staining of Recombinant Factor VIII Is Reduced in Apoptosis Resistant BHK-21 Cells, Journal of Biotechnology, 137 (2008), pp. 20-27.
Adamson, R., Annals of Hematology, "Design and Operation of a Recombinant Mammalian Cell Manufacturing Process for RFVIII", 1994, vol. 68, No. , pp. S9-S14.
Alberts et al, Garland Publishing and Inc, "Molecular Biology of the Cell Second Edition", 1989, p. 285.
European Patent 1863920, "Arguments in Support of Notice of Opposition by Novo Nordisk A/S dated Aug. 23, 2011," pp. 1-8.
Gilbert et al, Journal of Biological Chemistry, "Four Hydrophobic Amino Acids of the Factor VIII C2 Domain are Constituents of Both the Membrane-Binding and von Willebrand Factor-binding Motifs", 2002, vol. 277, No., pp. 6374-6381.
V.S. Purohit, -, "Immunogenicity of Recombinant Human Factor VFFL: Influence of Protein Aggregation and Excipients", 2005.
Notice of Opposition filed in European Patent 2144929 by Baxter Healthcare S.A., dated Oct. 11, 2012.
ChemSpider, Search and Share Chemistry, http://ChemSpider.com, 9 pages.

* cited by examiner

Factor VIII gene sequence (cDNA) (SEQ ID NO. 1):

atggaaatagagctctccacctgcttctttctgtgccttttgcgattctgcttagtgccaccagaagatactacctggggtgcagtggaa
ctgtcatgggactatatgcaaagtgatctcggtgagctgcctgtggacgcaagatttcctcctagagtgccaaaatctttccattcaac
acctcagtcgtgtacaaaaagactctgtttgtagaattcacggatcaccttttcaacatcgctaagccaaggccaccctggatggtct
gctaggtcctaccatccaggctgaggtttatgatacagtggtcattacacttaagaacatggcttcccatcctgtcagtcttcatgctgtt
ggtgtatcctactgaaagcttctgagggagctgaatatgatgatcagaccagtcaaaggagagaaagaagatgataaagtcttccc
tggtggaagccatacatatgtctggcaggtcctgaaagagaatggtccaatggcctctgacccactgtgccttacctactcatatctttc
tcatgtggacctggtaaaagacttgaattcaggcctcattggagccctactagtatgtagagaagggagtctggccaaggaaaaga
cacagaccttgcacaaatttatactacttttgctgtatttgatgaagggaaaagttggcactcagaaacaaagaactccttgatgcag
gataggatgctgcatctgctcggcctggcctaaaatgcacacagtcaatggttatgtaaacagtctctgccaggtctgattggat
gccacaggaaatcagtctattggcatgtgattggaatgggcaccactcctgaagtgcactcaatattcctcgaaggtcacacatttctt
gtgaaggaaccatcgccaggcgtcttggaaatctcgccaataacttttcctactgctcaaacactcttgatggaccttgacagtttcta
ctgttttgtcatatctcttccaccaacatgatggcatggaagcttatgtcaaagtagacagctgtccagaggaacccaactacgaat
gaaaaataatgaagaagcggaagactatgatgatgatctactgattctgaaatggatgtggtcaggtttgatgatgacaactctcct
tcctttatccaaattcgctcagttgccaagaagcatcctaaaactgggtacattacattgctgctgaagaggaggactgggactatgc
tcccttagtcctcgccccgatgacagaagttataaaagtcaatatttgaacaatggccctcagcggattggtaggaagtacaaaaa
agtccgatttatggcatacacagatgaaacctttaagactcgtgaagctattcagcatgaatcaggaatcttgggacctttactttatg
gggaagttggagacacactgttgattatatttaagaatcaagcaagcagaccatataacatctaccctcacggaatcactgatgtccg
tcctttgtattcaaggagattaccaaaaggtgtaaaacatttgaaggattttccaattctgccaggagaaatattcaaatataaatgga
cagtgactgtagaagatggccaactaaatcagatcctcggtgcctgacccgctattactctagtttcgttaatatggagagagatcta
gcttcaggactcattggccctctcctcatctgctacaagaatctgtagatcaaagaggaaaccagataatgtcagacaagaggaat
gtcatcctgtttctgtatttgatgagaaccgaagctggtacctcacagagaatatacaacgcttctcccccaatccagctggagtgcag
cttgaggatccagagttccaagcctccaacatcatgcacagcatcaatggctatgttttgatagtttgcagtgtcagtttgtttgcatg
aggtggcatactggtacattctaagcattggagcacagactgacttcctttctgtcttcttctctggatataccttcaaacacaaaatggt
ctatgaagacacactcacctattcccattctcaggagaaactgtcttcatgtcgatggaaaacccaggtctatggattctggggtgcc
acaactcagactttcggaacagaggcatgaccgccttactgaaggtttctagttgtgacaagaacactggtgattattacgaggaca
gttatgaagatatttcagcatacttgctgagtaaaacaatgccattgaaccaagaagcttctcccagaattcgcgacaccctagcact
aggcaaaagcaatttaatgccaccccaccggtcttgaaacgccatcaacgggagatcactcgtactactcttcagtctgatcaagag
gaaattgactatgatgataccatatcagttgaaatgaagaaggaagattttgacatttatgatgaggatgaaaatcagagccccgc
agctttcaaaagaaaacacgacactattttattgctgcagtggagaggctctggattatgggatgagtagctcccacatgttctaa
gaaacagggctcagagtggcagtgtccctcagttcaagaaagttgttttccaggaattactgatggctcttactcagcccttataccc
gtggagaactaaatgaacatttgggactcctggggccatatataagagcagaagttgaagataatatcatggtaactttcagaaatc
aggcctctcgtccctattccttctattctagccttatttcttatgaggaagatcagaggcaaggagcagaacctagaaaaaactttgtca
agcctaatgaaaccaaaacttactttttggaaagtgcaacatcatatggcaccccactaaagatgagtttgactgcaaagcctgggc

Figure 1 ttatttctctgatgttgacctggaaaaagatgtgcactcaggcctgattggaccccttctggtctgccacactaacacactgaaccctgc
tcatgggagacaagtgacagtacaggaatttgctctgtttttcaccatctttgatgagaccaaaagctggtacttcactgaaaatatgg
aaagaaactgcagggctccctgcaatatccagatggaagatcccacttttaaagagaattatcgcttccatgcaatcaatggctacat
aatggatacactacctggcttagtaatggctcaggatcaaaggattcgatggtatctgctcagcatgggcagcaatgaaaacatcca
ttctattcatttcagtggacatgtgttcactgtacgaaaaaaagaggagtataaaatggcactgtacaatctctatccaggtgttttga
gacagtggaaatgttaccatccaaagctggaatttggcgggtggaatgccttattggcgagcatctacatgctgggatgagcacact
ttttctggtgtacagcaataagtgtcagactccctgggaatggcttctggacacattagagatttcagattacagcttcaggacaata
tggacagtgggcccaaagctggccagacttcattattccggatcaatcaatgcctggagcaccaaggagccctttctcttggatcaag
gtggatctgttggcaccaatgattattcacggcatcaagacccagggtgcccgtcagaagttctccagcctctacatctctcagtttatc
atcatgtatagtcttgatgggaagaagtggcagacttatcgaggaaattccactggaaccttaatggtcttctttggcaatgtggattc
atctgggataaaacacaatattttttaacccctccaattattgctcgatacatccgtttgcacccaactcattatagcattcgcagcactcttc
gcatggagttgatgggctgtgatttaaatagttgcagcatgccattgggaatggagagtaaagcaatatcagatgcacagattactg
cttcatcctactttaccaatatgtttgccacctggtctccttcaaaagctcgacttcacctccaagggaggagtaatgctggagacctc
aggtgaataatccaaaagagtggctgcaagtggacttccagaagacaatgaaagtcacaggagtaactactcagggagtaaaatc
tctgcttaccagcatgtatgtgaaggagttcctcatctccagcagtcaagatggccatcagtggactctcttttttcagaatggcaaagt
aaaggttttttcagggaaatcaagactccttcacacctgtggtgaactctctagacccaccgttactgactcgctaccttcgaattcaccc
ccagagttgggtgcaccagattgccctgaggatggaggttctggctgcgaggcacaggacctctactga

Figure 1 (CONT.)

FACTOR VIII POLYPEPTIDE TITERS IN CELL CULTURES

CROSS-REFERENCE TO RELATED APPLICATIONS

This application is a 35 U.S.C. § 371 national stage application of International Patent Application PCT/EP2008/055349 (published as WO 2008/135501), filed Apr. 30, 2008, which claimed priority of European Patent Application 07107477.7, filed May 4, 2007; this application further claims priority under 35 U.S.C. § 119 of U.S. Provisional Application 60/928,302, filed May 9, 2007.

FIELD OF THE INVENTION

The present invention relates to a method for the production of a Factor VIII polypeptide involving the use of a C2-domain ligand, in particular O-Phospho-L-Serine (OPLS).

INCORPORATION-BY-REFERENCE OF THE SEQUENCE LISTING

In accordance with 37 C.F.R. § 1.52(e)(5), Applicants enclose herewith the Sequence Listing for the above-captioned application entitled "SEQUENCE LISTING", created on Oct. 19, 2009. The Sequence Listing is made up of 7 kilobytes, and the information contained in the attached "SEQUENCE LISTING" is identical to the information in the specification as originally filed. No new matter is added.

BACKGROUND OF THE INVENTION

Classic haemophilia or haemophilia A is an inherited bleeding disorder. It results from a chromosome X-linked deficiency of blood coagulation Factor VIII and affects almost exclusively males with an incidence of between one and two individuals per 10,000. The X-chromosome defect is transmitted by female carriers who are not themselves haemophiliacs. The clinical manifestation of haemophilia A is an increased bleeding tendency. Before treatment with Factor VIII concentrates was introduced the mean life span for a person with severe haemophilia was less than 20 years. The use of concentrates of Factor VIII from plasma has considerably improved the situation for the haemophilia patients increasing the mean life span extensively, giving most of them the possibility to live a more or less normal life. However, there have been certain problems with the plasma-derived concentrates and their use, the most serious of which have been the transmission of viruses. So far, viruses causing AIDS, hepatitis B, and non-A non-B hepatitis have hit the population seriously. Since then different virus inactivation methods and new highly purified Factor VIII concentrates have recently been developed which established a very high safety standard also for plasma derived Factor VIII.

Factor VIII (FVIII) is known to be expressed at very low levels in mammalian cells. Also, Factor VIII is known to be an unstable protein in serum-free or protein free medium. Addition of various substances has been used to improve the stability and titers of Factor VIII.

WO 9743436 discloses the addition of inhibitors of metal dependent inhibitors and/or chymotrypsins.

WO 88/08035 and WO 87/04187 disclose the addition of phospholipids to Factor VIII culture medium. Also the co-expression of von Willebrand Factor (vWF) is described.

US 2005 0227913 A1 discloses OPLS as an inhibitor of aggregation of Factor VIII by binding to the C2-domain (2303-2332). The less aggregated Factor VIII is claimed to be less immunogenic.

K. Hansen, M. Kjalke, P. B. Rasmussen, L. Kongerslev, and M. Ezban, Cytotechnol. 24 (3), 227-234, 1997, disclose the use of Bacitracin A and phosphatidylserine to prevent degradation of Factor VIII in medium.

WO 90/02175 A1 discloses processes producing recombinant polypeptide(s) by culturing eukaryotic cells in presence of protease inhibitors to prevent degradation of polypeptide(s).

EP 1707634 A1 discloses that substantial amounts of Factor VIII is associated with the cell surface and can be removed by washing with buffers of high ionic strength.

This being, there is still a need for improved production methods so as to improve the overall yield of Factor VIII polypeptides and/or reduce production costs.

SUMMARY OF THE INVENTION

A first aspect of the invention relates to a method for the production of a Factor VIII polypeptide, the method comprising the steps of a) culturing a mammalian cell expressing a Factor VIII polypeptide under conditions for expression of said Factor VIII polypeptide, said culturing conditions involving a cell culture medium comprising a C2-domain ligand, and b) isolating the expressed Factor VIII polypeptide from the mammalian cell by suitable means.

A second aspect of the invention relates to a method for the production of a Factor VIII polypeptide, the method comprising the steps of a) culturing a mammalian cell expressing a Factor VIII polypeptide under conditions for expression of said Factor VIII polypeptide, said culturing conditions involving a cell culture medium, and b) isolating the expressed Factor VIII polypeptide from the mammalian cell by suitable means, said suitable means involving the addition of a C2-domain ligand to said cells.

BRIEF DESCRIPTION OF THE FIGURES

FIG. 1. Factor VIII gene sequence (cDNA) (SEQ ID NO. 1).

DETAILED DESCRIPTION OF THE INVENTION

Figure 2A:
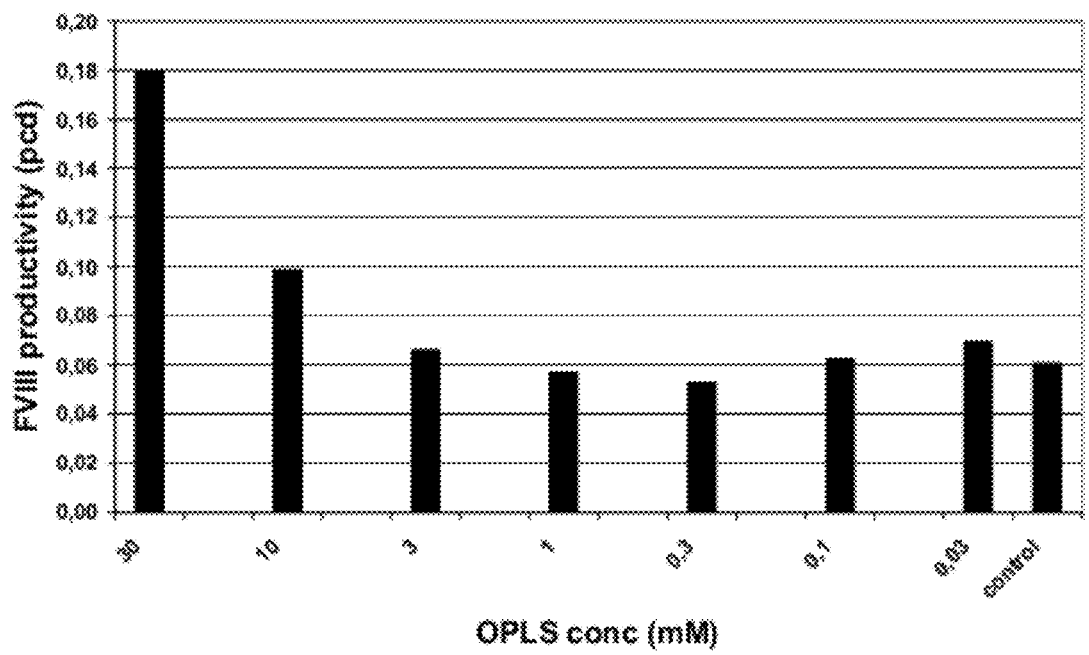
FIG. 2A-B: Effect of O-phospho-L-serine on FVIII productivity and FVIII protein specific activity.

As mentioned above, a first aspect of the invention relates to a method for the production of a Factor VIII polypeptide, the method comprising the steps of a) culturing a mammalian cell expressing a Factor VIII polypeptide under conditions for expression of said Factor VIII polypeptide, said culturing conditions involving a cell culture medium comprising a C2-domain ligand, and b) isolating the expressed Factor VIII polypeptide from the mammalian cell by suitable means.

A second aspect of the invention relates to a method for the production of a Factor VIII polypeptide, the method comprising the steps of a) culturing a mammalian cell expressing a Factor VIII polypeptide under conditions for expression of said Factor VIII polypeptide, said culturing conditions involving a cell culture medium, and b) isolating the expressed Factor VIII polypeptide from the mammalian cell by suitable means, said suitable means involving the addition of a C2-domain ligand to said cells.

In both instances, the C2-domain ligand plays an important role in facilitating an increased Factor VIII polypeptide titer levels in the cell culture medium.

Without being bound by any particular theory, it is believed that the increase in Factor VIII polypeptide titer levels in the cell culture medium is caused by the C2-domain ligand (in particular O-phospho-L-serine (OPLS)) that, either alone or in combination with a Soybean trypsin inhibitor (SBTI) and/or a plant protein hydrolysate, either (i) increases the amount of Factor VIII polypeptide secreted by the cells, and/or (ii) competes cell-bound Factor VIII polypeptide off the cells, and/or (iii) diminishes the degradation of Factor VIII polypeptide and thereby increases the amount of functional Factor VIII polypeptide present in the supernatant.

The invention will be explained in further details in the following.

The C2-domain ligand is a ligand capable of binding to or being bound to the C2-domain (see below) of the Factor VIII polypeptide. Preferably, the C2-domain ligand should be capable of displacing (competing off) the Factor VIII polypeptide from the cell membrane.

In the currently most preferred embodiment, the C2-domain ligand is O-Phospho-L-Serine (OPLS), i.e. a molecule of the formula $(HO)_2P(O)OCH_2CH(NH_2)CO_2H$.

Suitable alternative C2-domain ligands are believed to be the ones having the formula $(XO)(HO)P(O)OCH_2CH(NH_2)CO_2H$, wherein X is selected from optionally substituted $C_{1-6}$-alkyl, optionally substituted $C_{2-6}$-alkenyl, optionally substituted phenyl, optionally substituted heteroaryl, optionally substituted heterocyclyl, and optionally substituted benzyl. In one embodiment thereof, X is selected from optionally substituted $C_{1-6}$-alkyl, optionally substituted benzyl, and optionally substituted $C_{2-6}$-alkenyl.

In the present context, the term "$C_{1-6}$-alkyl" is intended to mean a linear, cyclic or branched hydrocarbon group having 1 to 6 carbon atoms, such as methyl, ethyl, propyl, isopropyl, pentyl, cyclopentyl, hexyl, cyclohexyl.

Similarly, the term "$C_{2-6}$-alkenyl" is intended to mean linear, cyclic or branched hydrocarbon groups having 2 to 6 carbon atoms and comprising at least one unsaturated bond. Examples of alkenyl groups are vinyl, allyl, butenyl, pentenyl, and hexenyl. Preferred examples of alkenyl are vinyl, allyl, butenyl, especially allyl.

In the present context, i.e. in connection with the terms "alkyl" and "alkenyl", the term "optionally substituted" is intended to mean that the group in question may be substituted one or several times, preferably 1-3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkylcarbonyl, formyl, aryl, aryloxy, arylamino, arylcarbonyl, heteroaryl, heteroaryloxy, heteroarylamino, heteroarylcarbonyl, heterocyclyl, heterocyclyloxy, heterocyclylamino, heterocyclylcarbonyl, amino, mono- and di($C_{1-6}$-alkyl)amino; carbamoyl, mono- and di($C_{1-6}$-alkyl) aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio, halogen, where any aryl, heteroaryl and heterocyclyl may be substituted as specifically described below for aryl, heteroaryl and heterocyclyl.

The term "halogen" includes fluoro, chloro, bromo, and iodo.

In the present context, the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaryl groups are benzimidazolyl, oxazolyl, isoxazolyl, thiazolyl, isothiazolyl, pyrrolyl, imidazolyl, pyrazolyl, pyridinyl, pyrimidinyl, pyrazinyl, pyridazinyl, furyl, thienyl, quinolyl, triazolyl, tetrazolyl, isoquinolyl, indolyl in particular benzimidazolyl, pyrrolyl, imidazolyl, pyridinyl, pyrimidinyl, furyl, thienyl, quinolyl, tetrazolyl, and isoquinolyl.

The term "heterocyclyl" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclyl groups (named according to the rings) are tetrahydrofuran, imidazolidine, piperazine, hexahydropyridazine, hexahydropyrimidine, diazepane, pyrrolidine, piperidine, azepane, oxazinane (morpholine), and thiazinane.

In the present context, i.e. in connection with the terms "aryl", "benzyl", "heteroaryl", "heterocyclyl" and the like (e.g. "aryloxy", "hetarylcarbonyl", etc.), the term "optionally substituted" is intended to mean that the group in question may be substituted one or several times, preferably 1-5 times, in particular 1-3 times, with group(s) selected from hydroxy, $C_{1-6}$-alkyl, $C_{1-6}$-alkoxy, oxo (which may be represented in the tautomeric enol form), carboxy, $C_{1-6}$-alkylcarbonyl, formyl, amino, mono- and di($C_{1-6}$-alkyl) amino; carbamoyl, mono- and di($C_{1-6}$-alkyl)aminocarbonyl, amino-$C_{1-6}$-alkyl-aminocarbonyl, $C_{1-6}$-alkylcarbonylamino, guanidino, carbamido, $C_{1-6}$-alkyl-sulphonyl-amino, arylsulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, sulphanyl, amino, amino-sulfonyl, mono- and di($C_{1-6}$-alkyl) amino-sulfonyl or halogen, where any alkyl, alkoxy and the like, representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidino.

In the most interesting embodiments (pertaining to both of the first and the second aspects of the invention), the C2-domain ligand (e.g. OPLS) is present in the cell culture medium in a concentration of 0.1-100 mM, such as 5-30 mM, in particular 10-20 mM.

Also interesting are the embodiments (pertaining to both of the first and the second aspects of the invention) wherein the C2-domain ligand is added to the cells in step b) in a concentration of 1-200 mM, such as 50-150 mM, in particular 70-130 mM.

The details for the production steps will be discussed in detail further below.

This being said, it has been found that a soybean trypsin inhibition (SBTI) may advantageously be combined with the C2-domain ligand in the cell culture medium in step a). Hence in a currently preferred embodiment, the cell culture medium further comprises a soybean trypsin inhibitor.

Soybean trypsin inhibitor is isolated from *Glycine max*. Soybean trypsin inhibitor from soybeans is a monomeric protein containing 181 amino acid residues in a single polypeptide chain cross-linked by two disulfide bridges. The molecular weight determined from the amino acid sequence is 20.1 kDa. Soybean trypsin inhibitor inhibits its target protease by forming a 1:1 stoichiometric complex.

In the most typical embodiments, the concentration of the soybean trypsin inhibitor in the cell culture medium is 0.01-100 mg/mL, such as 0.1-10 mg/mL, in particular 0.3-3 mg/mL.

It has also been found that a plant protein hydrolysate (sometime referred to as a "plant-derived digest", or the like) may advantageously be combined with the C2-domain ligand (and possibly also the soybean trypsin inhibitor) in the cell culture medium in step a). Hence, in a currently equally preferred embodiment, the cell culture medium further comprises plant protein hydrolysate.

The plant protein hydrolysate can be obtained from one of various sources, e.g. commercial sources. Typical types of hydrolysates are soy protein hydrolysate, wheat protein hydrolysates, pea protein hydrolysate, rice protein hydrolysate, etc. WO 01/23527 A1, which is hereby incorporated by reference, discloses the preparation and general use of a soy protein hydrolysate.

In the most typical embodiments, the concentration of the plant protein hydrolysate in the cell culture medium is 0.1-100 mg/mL, such as 1-10 mg/mL, in particular 2-7 mg/mL.

Factor VIII Polypeptide

The invention is adapted for the production of a Factor VIII polypeptide in a mammalian cell.

The mature Factor VIII molecule consists of 2332 amino acids which can be grouped into three homologous A domains, two homologous C domains and a B Domain which are arranged in the order: A1-A2-6-A3-C1-C2. During its secretion into plasma Factor VIII is processed intracellularly into a series of metal-ion linked heterodimers as single chain Factor VIII is cleaved at the B-A3 boundary and at different sites within the 6-domain. This processing leads to a heavy chain consisting of the A1, the A2 and various parts of the B-domain which has a molecular size ranging from 90 kDa to 200 kDa. The heavy chains are bound via a metal ion to the light chain, which consists of the A3, the C1 and the C2 domain (Saenko et al. 2002). In plasma this heterodimeric Factor VIII binds with high affinity to von Willebrand Factor, which protects it from premature catabolism. The half-life of non-activated Factor VIII bound to vWF is about 12 hours in plasma.

During the blood coagulation process Factor VIII is activated via proteolytic cleavage by FXa and thrombin at amino acids Arg372 and Arg740 within the heavy chain and at Arg1689 in the light chain resulting in the release of von Willebrand Factor and generating the activated Factor VIII heterotrimer which will form the tenase complex on phospholipid surfaces with FIXa and FX provided that $Ca^{2+}$ is present. The heterotrimer consists of the A1 domain, a 50 kDa fragment, the A2 domain a 43 kDa fragment and the light chain (A3-C1-C2), a 73 kDa fragment. Thus the active form of Factor VIII (Factor VIIIa) consists of an A1-subunit associated through the divalent metal ion linkage to a thrombin-cleaved A3-C1-C2 light chain and a free A2 subunit relatively loosely associated with the A1 and the A3 domain.

A Factor VIII molecule consisting of the heavy chain (HC) and light chain (LC) of Factor VIII connected with a small linker derived from the B-domain (B-domain deleted Factor VIII or BDD-FVIII) retains the biological activity of full length (native) Factor VIII.

In practicing the method of the present invention, any Factor VIII polypeptide that is therapeutically useful, e.g. effective in preventing or treating bleeding, may be relevant. This includes, without limitation, wild-type human Factor VIII, hybrid human/porcine Factor VIII and B-domain deleted human Factor VIII.

As used herein, "Factor VIII polypeptide" encompasses, without limitation, Factor VIII, as well as Factor VIII-related polypeptides.

The term "Factor VIII" is intended to encompass, without limitation, polypeptides having the amino acid sequence as described in Toole et al., Nature 1984, 312: 342-347 (wild-type human Factor VIII), as well as wild-type Factor VIII derived from other species, such as, e.g., bovine, porcine, canine, murine, and salmon Factor VIII. It further encompasses natural allelic variations of Factor VIII that may exist and occur from one individual to another. Also, degree and location of glycosylation or other post-translation modifications may vary depending on the chosen host cells and the nature of the host cellular environment. The term "Factor VIII" is also intended to encompass Factor VIII polypeptides in their uncleaved (zymogen) form, as well as those that have been proteolytically processed to yield their respective bioactive forms, which may be designated Factor VIIIa.

"Factor VIII-related polypeptides" include, without limitation, Factor VIII polypeptides that have either been chemically modified relative to human Factor VIII (i.e. Factor VIII derivatives) and/or contain one or more amino acid sequence alterations relative to human Factor VIII (i.e., Factor VIII variants), and/or contain truncated amino acid sequences relative to human Factor VIII (i.e., Factor VIII fragments). Such Factor VIII-related polypeptides may exhibit different properties relative to human Factor VIII, including stability, phospholipid binding, altered specific activity, and the like. The term "Factor VIII-related polypeptides" are intended to encompass such polypeptides in their uncleaved (zymogen) form, as well as those that have been proteolytically processed to yield their respective bioactive forms, which may be designated "Factor VIIIa-related polypeptides" or "activated Factor VIII-related polypeptides".

As used herein, "Factor VIII-related polypeptides" also encompasses, without limitation, polypeptides exhibiting substantially the same or improved biological activity relative to wild-type human Factor VIII, as well as polypeptides, in which the Factor VIII biological activity has been substantially modified or reduced relative to the activity of wild-type human Factor VIII. These polypeptides include, without limitation, Factor VIII or Factor VIIIa that has been chemically modified and Factor VIII variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human Factor VIII.

Factor VIII-related polypeptides, including variants of Factor VIII, whether exhibiting substantially the same or better bioactivity than wild-type Factor VIII, or, alternatively, exhibiting substantially modified or reduced bioactivity relative to wild-type Factor VIII, include, without limitation, polypeptides having an amino acid sequence that differs from the sequence of wild-type Factor VIII by insertion, deletion, or substitution of one or more amino acids.

Factor VIII-related polypeptides, including variants, encompass those that exhibit at least about 10%, at least about 20%, at least about 30%, at least about 40%, at least about 50%, at least about 60%, at least about 70%, at least about 80%, at least about 90%, at least about 100%, at least about 110%, at least about 120%, and at least about 130%, of the specific activity of wild-type factor VIII that has been produced in the same cell type, when tested in the factor VIII activity assay as described in the present specification.

Factor VIII-related polypeptides, including variants, having substantially the same or improved biological activity relative to wild-type factor VIII encompass those that exhibit at least about 25%, such as at least 50%, at least 75%, or at least 90% of the specific biological activity of wild-type human factor VIII that has been produced in the same cell type when tested in one or more of the specific factor VIII activity assay as described below in the present description ("Materials and Methods").

Factor VIII-related polypeptides, including variants, having substantially reduced biological activity relative to wild-type factor VIII are those that exhibit less than about 25%, such as less than about 10%, or less than about 5% of the specific activity of wild-type factor VIII that has been produced in the same cell type when tested in one or more of the specific factor VIII activity assays as described below in the present description ("Materials and Methods").

Non-limiting examples of Factor VIII polypeptides include plasma-derived human Factor VIII as described, e.g., in Fulcher et al.; Proc. Acad. Nat. Sci. USA 1982; 79:1648-1652, and Rotblat et al.; Biochemistry 1985; 24:4294-4300, and plasma-derived porcine FVIII as described, e.g., in Fass et al.; Blood 1982; 59: 594-600 and Knutson et al.; Blood 1982; 59: 615-624. Non-limiting examples of Factor VIII sequence variants are described, e.g., in Lollar et al.; Blood 2000; 95(2): 564-568 (hybrid porcine/human FVIII polypeptides) and Lollar et al.; Blood 2001; 97(1): 169-174.

The cloning of the cDNA for Factor VIII (Wood, W. I., et al. (1984) Nature 312, 330-336; Vehar, G. A., et al. (1984) Nature 312, 337-342) made it possible to express Factor VIII recombinantly leading to the development of several recombinant Factor VIII products, which were approved by the regulatory authorities between 1992 and 2003. The coding sequence for Factor VIII (cDNA) is shown in FIG. 1. The fact that the central B domain of the Factor VIII polypeptide chain residing between amino acids Arg-740 and Glu-1649 does not seem to be necessary for full biological activity has also led to the development of a B-domain deleted Factor VIII. See also Kjalke M, Heding A, Talbo G, Persson E, Thomsen J and Ezban M (1995), "Amino acid residues 721-729 are required for full Factor VIII activity". Eur. J. Biochem: 234: 773-779.

Step a)—Transfection and Culturing of Cells

Cells

The mammalian cell expressing the Factor VIII polypeptide is typically selected from the group consisting of mammalian cells that endogenously express the Factor VIII polypeptide and mammalian cells that have been transfected with a gene for the Factor VIII polypeptide.

In one currently interesting embodiment of the latter, the mammalian cell has been transfected with an expression vector comprising a nucleic acid molecule encoding the Factor VIII polypeptide and expression control regions operatively linked to thereto.

Expression of protein in cells is well-known to the person skilled in the art of protein production. In practicing the present invention, the cells are mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk$^-$ ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk$^-$ ts13 BHK cell line is also available from the ATCC under accession number CRL 1632. Preferred CHO cell lines are the CHO K1 cell line available from ATCC under accession number CCI61, as well as cell lines CHO-DXB11 and CHO-DG44.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

Cell Culturing

In some embodiments, the cells used in practicing the invention are capable of growing in suspension cultures. As used herein, suspension-competent cells are those that can grow in suspension without making large, firm aggregates, i.e., cells that are monodisperse or grow in loose aggregates with only a few cells per aggregate. Suspension-competent cells include, without limitation, cells that grow in suspension without adaptation or manipulation (such as, e.g., hematopoietic cells or lymphoid cells) and cells that have been made suspension-competent by gradual adaptation of attachment-dependent cells (such as, e.g., epithelial or fibroblast cells) to suspension growth.

The cells used in practicing the invention may be adhesion cells (also known as anchorage-dependent or attachment-dependent cells). As used herein, adhesion cells are those that need to adhere or anchor themselves to a suitable surface for propagation and growth. In one embodiment of the invention, the cells used are adhesion cells. In these embodiments, both the propagation phases and the production phase include the use of microcarriers. The used adhesion cells should be able to migrate onto the carriers (and into the interior structure of the carriers if a macroporous carrier is used) during the propagation phase(s) and to migrate to new carriers when being transferred to the production bioreactor. If the adhesion cells are not sufficiently able to migrate to new carriers by themselves, they may be liberated from the carriers by contacting the cell-containing microcarriers with proteolytic enzymes or EDTA. The medium used (particularly when free of animal-derived components) should furthermore contain components suitable for supporting adhesion cells; suitable media for cultivation of adhesion cells are available from commercial suppliers, such as, e.g., Sigma.

The cells may also be suspension-adapted or suspension-competent cells. If such cells are used, the propagation of cells may be done in suspension, thus microcarriers are only used in the final propagation phase in the production culture vessel itself and in the production phase. In case of suspension-adapted cells the microcarriers used are typically macroporous carriers wherein the cells are attached by means of physical entrapment inside the internal structure of the carriers. However, in case of such suspension-adapted cells, both propagation of cells and production may be done in suspension.

In such embodiments, the mammalian cell is typically selected from CHO, BHK, HEK293, myeloma cells, etc.

Cell Culture Medium

Besides the components mentioned above, i.e. the C2-domain ligand (required for the invention pertaining to the first aspect of the invention), the optional soybean trypsin inhibition, and the optional plant protein hydrolysate, the cell culture medium includes a number of other constituents which—as the skilled person will know—are necessary for the propagation of the cells and production of the Factor VIII polypeptide.

The term "cell culture medium" (or simply "medium") refers to a nutrient solution used for growing mammalian cells that typically provides at least one component from one or more of the following categories: (1) salts of e.g. sodium, potassium, magnesium, and calcium contributing to the osmolality of the medium; (2) an energy source, usually in the form of a carbohydrate such as glucose; (3) all essential amino acids, and usually the basic set of twenty amino acids; (4) vitamins and/or other organic compounds required at low concentrations; and (5) trace elements, where trace elements are defined as inorganic compounds that are typically required at very low concentrations, usually in the micromolar range. The nutrient solution may optionally be supplemented with one or more of the components from any of the following categories: (a) hormones and other growth factors such as, for example, insulin, transferrin, and epidermal growth factor; and (b) hydrolysates of protein and tissues. Preferably, the cell culture medium does not contain any components of animal origin.

The present invention encompasses cultivating mammalian cells in medium lacking animal-derived components. As used herein, "animal-derived" components are any components that are produced in an intact animal (such as, e.g., proteins isolated and purified from serum), or produced by using components produced in an intact animal (such as, e.g., an amino acid made by using an enzyme isolated and purified from an animal to hydrolyze a plant source material). By contrast, a protein which has the sequence of an animal protein (i.e., has a genomic origin in an animal) but which is produced in vitro in cell culture (such as, e.g., in a recombinant yeast or bacterial cell or in an established continuous mammalian cell line, recombinant or not), in media lacking components that are produced in, and isolated and purified from an intact animal is not an "animal-derived" component (such as, e.g., insulin produced in a yeast or a bacterial cell, or insulin produced in an established mammal cell line, such as, e.g., CHO, BHK or HEK cells, or interferon produced in Namalwa cells). For example, a protein which has the sequence of an animal protein (i.e., has a genomic origin in an animal) but which is produced in a recombinant cell in media lacking animal derived components (such as, e.g., insulin produced in a yeast or bacterial cell) is not an "animal-derived component". Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants. Any cell culture medium, in particular one lacking animal-derived components, that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. In one embodiment, the medium lacks animal-derived components and lacks proteins ("protein-free"). Media lacking animal-derived components and/or proteins are available from commercial suppliers, such as, for example, Sigma, JRH Biosciences, Gibco, Hyclone and Gemini.

In one embodiment, the cell culture medium is essentially serum free. In another embodiment, the medium is a medium lacking animal-derived components. In a further embodiment, the medium is lacking proteins ("protein-free") as well as lacking animal-derived components.

In one embodiment the medium is a commercially available CHO medium lacking animal-derived components, such as, e.g., EXCELL™ (SAFC Biosciences), PF-CHO, PF-CHO-LS, SFM4CHO, or CDM4CHO (all from Hyclone), and the cell line is a CHO cell.

In some embodiments, the cells used in practicing the present invention are adapted to suspension growth in medium lacking animal-derived components, such as, e.g., medium lacking serum. Such adaptation procedures are described, e.g., in Scharfenberg, et al., *Animal Cell Technology Developments towards the 21$^{st}$ Century*, E. C. Beuvery et al. (Eds.), Kluwer Academic Publishers, pp. 619-623, 1995 (BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a particularly preferred embodiment, the host cells are BHK 21 or CHO cells that have been engineered to express human Factor VIII and that have been adapted to grow in the absence of serum or animal-derived components.

Cell Culture Procedures

The methods of the invention are typically performed in a stirred culture vessel and a draw-fill process type is typically employed. In this process the cells are grown after inoculation, and when a certain density is reached, about 70% of the culture is harvested, and the remaining culture is supplied with fresh cell culture medium to its original volume. This is typically repeated about 2-10 times.

Alternatively, a microcarrier process type can be employed. In the microcarrier-based process the cells have migrated into the internal structure of the carriers (macroporous carriers) or have attached themselves to the surface of the carriers (solid carriers), or both. In a microcarrier-based process the mammalian cells, the microcarriers and the cell culture medium are supplied to a culture vessel initially. In the following days additional cell culture medium may be fed if the culture volume was not brought to the final working volume of the vessel from the start. During the following period periodic harvest of product-containing culture supernatant and replacement with new medium liquid is performed, until the culture is finally terminated. When harvesting product-containing supernatant the agitation, e.g., stirring, of the culture is stopped and the cell-containing carriers are allowed to sediment following which part of the product-containing cell culture supernatant is removed. In order to improve the overall outcome of the procedure, a cooling step may preferably be applied before harvesting of the product-containing supernatant, see, e.g., WO 03/029442. In some embodiments the cell culture medium is cooled to a temperature between about 18° C. and about 32° C. before allowing the carriers to sediment, or between about 20° C. and about 30° C., or between about 22° C. and about 28° C.

Other applicable variants of the cell culture procedure are described in WO 02/29084 (Novo Nordisk A/S).

Before reaching the production phase where regular harvesting of product-containing culture supernatant for further down-stream processing is performed, the cells are propagated according to any scheme or routine that may be suitable for the particular cell in question. The propagation phase may be a single step or a multiple step procedure. In a single step propagation procedure the cells are removed from storage and inoculated directly to the culture vessel (optionally containing microcarriers) where the production is going to take place. In a multiple step propagation procedure the cells are removed from storage and propagated through a number of culture vessels of gradually increasing size until reaching the final culture vessel (optionally containing microcarriers) where production is going to take place. During the propagation steps the cells are grown under conditions that are optimized for growth. Culture conditions, such as temperature, pH, dissolved oxygen tension, concentration of dissolved $CO_2$, and the like, are those known to be optimal for the particular cell and will be apparent to the skilled person or artisan within this field (see, e.g., *Animal Cell Culture: A Practical Approach* 2$^{nd}$ Ed., Rickwood, D. and Hames, B. D., eds., Oxford University Press, New York (1992)).

In one approach, the cell culture process is operated in one culture vessel: The cells are inoculated directly into the culture vessel (optionally containing microcarriers) where the production is going to take place; the cells are propagated until a suitable cell density is reached and the production phase is initiated.

In another approach, the cell culture process is operated in at least two distinct culture vessels: One or more seed culture vessel(s) (first propagation step(s)) followed by the production culture vessel (last propagation step followed by production phase). In the first propagation step the cells expressing the desired polypeptide are inoculated into a seed culture vessel containing the cell culture medium and propagated until the cells reach a minimum cross-seeding density. Subsequently, the propagated seed culture is transferred to the production culture vessel containing the cell culture medium and (optionally) microcarriers. In case of a process using microcarriers the cells are cultured in this culture vessel under conditions in which the cells migrate onto the surface of the solid carriers or the exterior and interior surfaces of the macroporous carriers, and they continue to grow in this last propagation step until the carriers are fully colonized by the cells. During this last propagation step medium exchange is performed by allowing the microcarriers to settle to the bottom of the culture vessel, after which a predetermined percentage of the tank volume is removed and a corresponding percentage tank volume of fresh medium is added to the vessel. The microcarriers are then re-suspended in the medium and this process of medium removal and replacement are repeated at a predetermined interval, for example every 24 hours. The amount of replaced medium depends on the cell density and may typically be from 10-95%, preferably from 25% to 80%, of the tank volume.

In case of a suspension process, e.g. a perfusion, batch or draw-fill process, the cells are grown freely suspended without being immobilised in carriers. In a suspension cell-perfusion process the cells are inoculated into a seed culture vessel containing culture medium lacking animal-derived components and propagated until the cells reach a minimum cross-seeding density. Subsequently, the propagated seed culture is transferred to a large-scale culture vessel containing culture medium lacking animal-derived components and propagated until at least a predetermined cell density is reached. In this phase the cells are grown in suspension to allow the cell number within the culture vessel to increase to a predetermined or critical value. The medium exchange is performed by continuously perfusing the culture vessel with fresh medium.

The amount of perfused medium depends on the cell density and may typically be from 10-95%, preferably from 25% to 80%, of the tank volume per day (24 hours). When the cell density reaches the value suitable for initiation of production phase, 60-95% of the tank medium in the tank is typically changed every 24 hours, such as e.g. about 80%. An 80% medium exchange is also preferably used in the production phase.

In a simple batch process the cells are inoculated into a seed culture vessel containing culture medium lacking animal-derived components and propagated until the cells reach a minimum cross-seeding density. Subsequently, the propagated seed culture is transferred to a large-scale culture vessel containing culture medium lacking animal-derived components.

A batch process such as this can be extended by feeding a concentrated solution of nutrients to the tank. This extends the process time and ultimately leads to an increase in FVII production within the culture vessel. The time of harvest has to be determined as a balance between the longest possible operation of the tank and the risk of cell lysis.

A simple Draw-Fill process closely resembles a repeated batch fermentation. In batch fermentation the cells grow in the culture vessel and the medium is harvested at the end of the run. In a Draw-Fill process the culture vessel is harvested before any of the nutrients become exhausted. Instead of removing all of the contents from the vessel, only a proportion of the tank volume is removed (typically 80% of the tank volume). After the harvest, the same volume of fresh medium is added back to the vessel. The cells are then allowed to grow in the vessel once more and another 80% harvest is taken a set number of days later. In repeated batch processes the cells left in the vessel after a harvest may be used as the inoculum for the next batch.

A Draw-Fill process is operated in two phases. The first phase of the process is operated identically to a simple batch process. After the first harvest, the culture vessel is again operated as a simple batch process; however, the length of the batch is shorter than the first batch because of the higher initial cell density. Theses short 'repeated batch phases' are continued indefinitely.

A fed-batch Draw-Fill is a draw-fill fermentation with a concentrated feed similar to the type proposed in the fed-batch process. A concern with a simple draw-fill process is that the fresh medium added may not be sufficient to sustain the cells over repeated batch fermentations. The inclusion of a feed would remove this worry. A feed would also allow operating the culture vessel with long batch times in a draw-fill process.

The culture vessel may be operated within a broad range of cycle times and a broad range of draw-fill volumes. Ranges and preferred values can be seen from Table 1, below.

TABLE 1

| Setpoint | Range | Preferred range | More preferred Value |
|---|---|---|---|
| Initial Batch Phase | | | |
| PH | 6-8 | 6.6-7.6 | 7.0 for CHO and 6.6-7.4 for BHK |
| Temperature | 28-40° C. | 30-37° C. | 37° C. for CHO and 36° C. for BHK |
| Temperature drop (OPTIONAL) | | | |
| Temperature drop to | 26-39° C. | 30-36° C. | 32° C. |
| Temperature drop at | $0.5$-$12.0 \times 10^6$ cells ml$^{-1}$ | $0.5$-$12.0 \times 10^6$ cells ml$^{-1}$ | $2.0$-$10 \times 10^6$ cells ml$^{-1}$ |
| DOT Harvest | 10-100% | 20-60% | 30% |
| Tank volume | 10-99% | 10-90% | 80% |
| Harvest time | 2-10 days. | 5-10 days. | 9 days after start |
| Feed initiated | 6-0 gl$^{-1}$ | 3-0 gl$^{-1}$ | When glucose <2 gl$^{-1}$ |
| Repeated Batch Phases | | | |
| PH | 6-8 | 6.6-7.6 | 7.0 for CHO and 6.6-7.4 for BHK |
| Temperature | 28-40° C. | 30-37° C. | 37° C. for CHO and 36° C. for BHK |
| Temperature drop (OPTIONAL) | | | |
| Temperature drop to | 26-39° C. | 30-36° C. | 32° C. |
| Temperature drop at | $0.5$-$12.0 \times 10^6$ cells ml$^{-1}$ | $0.5$-$12.0 \times 10^6$ cells ml$^{-1}$ | $2.0$-$10 \times 10^6$ cells ml$^{-1}$ |
| DOT Harvest | 10-100% | 20-60% | 30% |
| Tank volume | 10-99% | 10-90% | 80% |
| Harvest time | 1-7 days. | 1-7 days. | 5 days after harvest |
| Feed initiated | 3-0 gl$^{-1}$ | 3-0 gl$^{-1}$ | When glucose <2 gl$^{-1}$ |

It will be understood that in a process where the propagation phase is a multiple step procedure the propagation may take place in culture vessels of progressively increasing size until a sufficient number of cells is obtained for entering the final culture vessel. For example, one or more seed culture vessels of 5 L, 50 L, 100 L or 500 L may be used sequentially. A seed culture vessel typically has a capacity of between 5 L and 1000 L. Typically, cells are inoculated into a seed culture vessel at an initial density of about 0.2 to $0.4 \times 10^6$ cells/mL and propagated until the culture reaches a cell density of about $1.0 \times 10^6$ cells/mL. Typically, a minimum cross-seeding density is between about 0.8 and about $1.5 \times 10^6$ cells/mL.

Some of the set-points that are suitable for the production of Factor VIII are not necessarily suitable for the initial growth of the cells, either in seed culture or on the microcarriers. For example, temperature, dissolved oxygen tension, and/or pH may be different for the two phases. The medium exchanges during propagation is done to keep the cells alive and growing, not to harvest culture supernatant for down-stream processing.

Optionally, a drop in temperature set point of the cultivation may be employed when entering, and during, the production phase. Furthermore, when entering the production phase temperature, operating pH and medium exchange frequency are typically changed to values that are optimal for production.

Microcarriers

As used herein, microcarriers are particles which are small enough to allow them to be used in suspension cultures (with a stirring rate that does not cause significant shear damage to cells). They are solid, porous, or have a solid core with a porous coating on the surface. Microcarriers may, for example, without limitation, be cellulose- or dextran-based, and their surfaces (exterior and interior surface in case of porous carriers) may be positively charged. Further details can be found in WO 02/29083 and in "Microcarrier cell culture, principles and methods. Amersham Pharmacia Biotech. 18-1140-62. Edition AA".

Useful solid microcarriers include, without limitation, Cytodex 1™ and Cytodex 2™ (Amersham Pharmacia Biotech, Piscataway N.J.). Solid carriers are particularly suitable for adhesion cells (anchorage-dependent cells). Useful macroporous carriers include, without limitation, Cytopore 1™ and Cytopore 2™ (Amersham Pharmacia Biotech, Piscataway N.J.). Particularly preferred are Cytopore 1™ carriers, which have a mean particle diameter of 230 μm, an average pore size of 30 um, and a positive charge density of 1.1 meq/g.

Large-Scale Culture Conditions

The invention is particularly relevant for large-scale production. By the term "large-scale production" is meant production involving a culture vessel of at least 100 L. In preferred embodiments, however, the scale is typically at least 250 L, such as at least 500 L, e.g. at least 1000 L or even 5000 L or more. The term "large-scale" may be used interchangeably with the terms "industrial-scale" and "production-scale".

The method for large-scale production of the polypeptide is typically conducted over a period of at least 120 hours, e.g. 1-26 weeks.

In case that the cell culture process is operated in at least two distinct culture vessels, such as one or more seed culture vessel(s) (first propagation step(s)) followed by the production culture vessel (last propagation step followed by production phase), then the process typically involves transferring about 50 L of the propagated seed culture (having about $1.0 \times 10^6$ cells/mL) into a 500 L culture vessel containing 150 L of cell culture medium. The large-scale culture is maintained under appropriate conditions of, e.g., temperature, pH, dissolved oxygen tension (DOT), and agitation rate, and the volume is gradually increased by adding medium to the culture vessel. In case of a microcarrier process the culture vessel also comprises an amount of microcarriers corresponding to a final microcarrier concentration in the range of 1 to 10 g/L. After the transfer, the cells typically migrate onto the surface of the carriers or into the interior of the carriers within the first 24 hours.

Culture Vessel

Culture vessels applicable within the present invention may, e.g., be based on conventional stirred tank reactors (CSTR) where agitation is obtained by means of conventional impeller types or airlift reactors where agitation is obtained by means of introducing air from the bottom of the vessel. Among the further parameters that are typically controlled within specified limits are pH, dissolved oxygen tension (DOT), concentration of dissolved $CO_2$ and temperature. Dissolved oxygen tension may be maintained by, e.g., sparging with pure oxygen. The concentration of dissolved $CO_2$ may be maintained by sparging with air. The temperature-control medium is typically water, heated or cooled as necessary. The water may be passed through a jacket surrounding the vessel or through a piping coil immersed in the culture.

The term "culture vessel" may be used interchangeably with "tank", "reactor", "fermentor" and "bioreactor".

Step b)—Isolation of Expressed Polypeptide

In this step b), the Factor VIII polypeptide is to be isolated from the mammalian cells by suitable means. In a typical embodiment, the cells can be removed from the medium and the medium can be clarified by means of sequential filtration of harvest through 1.0 μm and 0.2 μm filters.

The Factor VIII in the medium (cell culture supernatant) may then advantageously be up-concentrated cation-exchange chromatography where Factor VIII rich fractions are pooled. The Factor VIII polypeptide may then be purified by binding to an anti-Factor VIII antibody column (e.g. an F25 antibody column, see, e.g., WO 95/13301 and for Nordfang et al. 1995 (Thromb. Haemostas. 54:586-590)) followed by elution under conditions that preserve the Factor VIII polypeptide activity. Further impurities may be removed by buffer exchange by gel-filtration.

According to the second aspect of the invention, but also useful in relating to the first aspect of the invention, a C2-domain ligand is added in order to facilitate the isolation of the Factor VIII polypeptide from the cells, i.e. the C2-domain ligand (e.g. OPLS) is added in order to liberate cell-bound Factor VIII polypeptide.

A particular feature of the present invention is that the Factor VIII polypeptide can be isolated from the cells without inactivation or destruction of the mammalian cells. Thus, in a particular embodiment, the expressed Factor VIII polypeptide is harvested from the cell culture medium substantially without reduction of the viability of the cells. Moreover, it is advantageous if the production can be continued using the same batch of cells.

Once the medium containing the Factor VIII polypeptide has been isolated from the cells, it may be subjected to one or more processing steps to purify the desired protein, including, without limitation, affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989.

Purification of Factor VIII polypeptides may in particular involve affinity chromatography on an anti-Factor VIII antibody column and activation by proteolytic cleavage.

The following examples are intended as non-limiting illustrations of the present invention.

EXAMPLES

Materials and Methods

Cell line: The cell line used for transfection, dhfr– CHO cells DUKX-B11 cells (Urlaub, G. & Chasin, L. A. (1980) Proc. Natl. Acad. Sci. USA 77, 4216-4220), was adapted to grow in suspension cultures using serum-free medium supplemented with ribonucleosides and deoxyribonucleosides.

Expression vector: Factor VIII transcription is achieved using an adenovirus-SV40 promoter and a selection by a di-hydrofolate reductase selection marker. The expressed Factor VIII molecule consist of the heavy chain (HC) and light chain (LC) of Factor VIII connected with a small linker derived from the B-domain. The B-domain has been removed, since this allows for higher expression of Factor VIII and the biological activity of Factor VIII is retained.

Transfection: The β-lactamase gene was removed by digestion with restriction enzymes from plasmid #815 F8-500B-pTSV7 and the resulting fragment containing the Factor VIII gene was gel purified and used for transfection of CHO DUKX-B11 cells using FuGENE 6 (Roche). Transfection was carried out in 6-well plates in α-MEM medium (Gibco) supplemented with ribonucleosides and deoxyribonucleosides and 10% dialyzed FBS. Two days after transfection the cells was transferred to TC80 flasks in α-MEM medium (Gibco) without ribonucleosides and deoxyribonucleosides but with 10% dialyzed FBS. After selection of surviving transfectants for 15 days stepwise amplification with MTX was started. Cells were amplified up to 1000 nM MTX with several sub-clonings being performed during this process.

SF adaptation and cell culturing: Cells were adapted to grow in serum free medium by stepwise reducing the concentration of FBS in the SF medium. Cells were adapted and maintained in 125 mL shaker flasks.

Cell culturing during serum free medium supplementation experiments: For media supplement experiments cells were cultivated in a high-cell density perfusion model in 50 mL shaker tubes with vented cap at 35° C. in serum free medium, as described below. Cells were cultivated in large shaker flasks at 37° C. Cell viability was measured at cell harvest, and this was always >95%. Harvested cells were re-suspended into fresh medium. 2.5 mL of the harvested and re-suspended cells was added to 2.5 mL of fresh medium containing the supplement to give a total volume of 5 mL, with a concentration of $1 \times 10^7$ cells/mL. Shaker tubes were then placed in shaker at 35° C. and 250 rpm. After 24 hours, samples were assayed for cell density, viability, CoA, ELISA and Factor VIII protein integrity by Western blot.

Cell viability: Viability of the cell culture may be measured, for example, as described in Mammalian Cell Culture; essential techniques, 1997 (Wiley) Editors: A. Doyle and J. Bryan Griffiths (see. e.g., protocols 13 and 14).

CoA assay (Factor VIII activity assay): In the presence of calcium and phospholipids, Factor X is activated to Factor Xa by Factor IXa. This generation is greatly stimulated by Factor VIII, which may be considered as a cofactor in this reaction. By using optimal amounts of $Ca^{2+}$ and phospholipids and an excess of Factors IXa and X, the rate of activation of Factor X is solely dependent on the amount of Factor VIII. Factor Xa hydrolyses the chromogenic substrate S-2765 thus liberating the chromophoric group, pNA. The colour is then read photometrically at 405 nm. The generated Factor Xa and thus the intensity of colour is proportional to the Factor VIII activity in the sample. Hydrolysis of S-2765 by thrombin formed is prevented by the addition of the synthetic thrombin inhibitor, I-2581, together with the substrate (Chromogenix Coatest SP Factor VIII, diaPharma)

Other tests for Factor VIII activity: Further suitable assays for detecting Factor VIII activity can be preformed as simple in vitro tests as described, for example, in Kirkwood T B L, Rizza C R, Snape T J, Rhymes I L, Austen D E G. Identification of sources of interlaboratory variation in factor VIII assay. B J Haematol 1981; 37; 559-68.; or Kessels et al., British Journal of Haematology, Vol. 76 (Suppl. 1) pp. 16 (1990)). Factor VIII biological activity may also be quantified by measuring the ability of a preparation to correct the clotting time of factor VIII-deficient plasma, e.g., as described in Nilsson et al., 1959. (Nilsson I M, Blombaeck M, Thilen A, von Francken I., Carriers of haemophilia A—A laboratory study, Acta Med Scan 1959; 165:357). In this assay, biological activity is expressed as units/ml plasma (1 unit corresponds to the amount of FVIII present in normal pooled plasma.

ELISA: Strip wells are pre-coated with sheep polyclonal antibody to human Factor VIII. Samples are diluted and applied to the wells. The Factor VIII antigen present binds to the coated antibody. After washing away unbound material, peroxidase-labeled sheep detecting antibody is applied and allowed to bind to the captured Factor VIII. The wells are again washed and a solution of TMB (the peroxidase substrate tetramethylbenzidine) is applied and allowed to react for a fixed period of time. A blue color develops which changes to yellow upon quenching the reaction with acid. The color formed is measured spectrophotometrically in a microplate reader at 450 nm. The absorbance at 450 nm is directly proportional to the quantity of Factor VIII antigen captured onto the well (VisuLize, FVIII antigen kit, Affinity biologicals). The assay is calibrated using purified B domain deleted Factor VIII.

F25 ELISA: ELISA: Strip wells are pre-coated with sheep polyclonal antibody to human Factor VIII. Samples are diluted and applied to the wells. The Factor VIII antigen present binds to the coated antibody. After washing away unbound material, diluted F25 mouse monoclonal anti-Factor VIII antibody recognizing the C-terminal of the Factor VIII heavy chain is applied and allowed to bind to the captured Factor VIII. The wells are again washed and diluted peroxydase-labeled goat anti-mouse IgG (DAKO) is applied and allowed to bind to the captured F25 antibody. The wells are again washed and a solution of TMB (the peroxidase substrate tetramethylbenzidine) is applied and allowed to react for a fixed period of time. A blue color develops which changes to yellow upon quenching the reaction with acid. The color formed is measured spectrophotometrically in a microplate reader at 450 nm. The absorbance at 450 nm is directly proportional to the quantity of Factor VIII antigen captured onto the well. The assay is calibrated using an in house standard of heavy chain Factor VIII that has been affinity purified with the F25 antibody.
(F25 antibody: See, e.g., WO 95/13301 and for Nordfang et al. 1995 (Thromb. Haemostas. 54:586-590).

Example 1

Supplementing Serum-Free cell Culture Medium of Factor VIII Producing Cells With OPLS OPLS was supplemented to serum free cell culture medium in the indicated concentration according to the experimental details described under materials and methods. The results can be seen from the below Table 3 and from FIGS. 2A and 2B.

TABLE 3

Supplementing serum-free cell culture medium of Factor VIII producing cells with OPLS

| OPLS Concentration (mM) | Factor VIII productivity (pcd)) | Factor VIII protein specific activity (U/microg)) |
| --- | --- | --- |
| 0 | 0.061 | 11.0 |
| 0.03 | 0.068 | 11.8 |

TABLE 3-continued

Supplementing serum-free cell culture medium of Factor VIII producing cells with OPLS

| OPLS Concentration (mM) | Factor VIII productivity (pcd)) | Factor VIII protein specific activity (U/microg)) |
| --- | --- | --- |
| 0.1 | 0.062 | 12.8 |
| 0.3 | 0.052 | 12.2 |
| 1 | 0.058 | 12.6 |
| 3 | 0.066 | 15.8 |
| 10 | 0.10 | 15.4 |
| 30 | 0.18 | 15.0 |

Figure 2B:
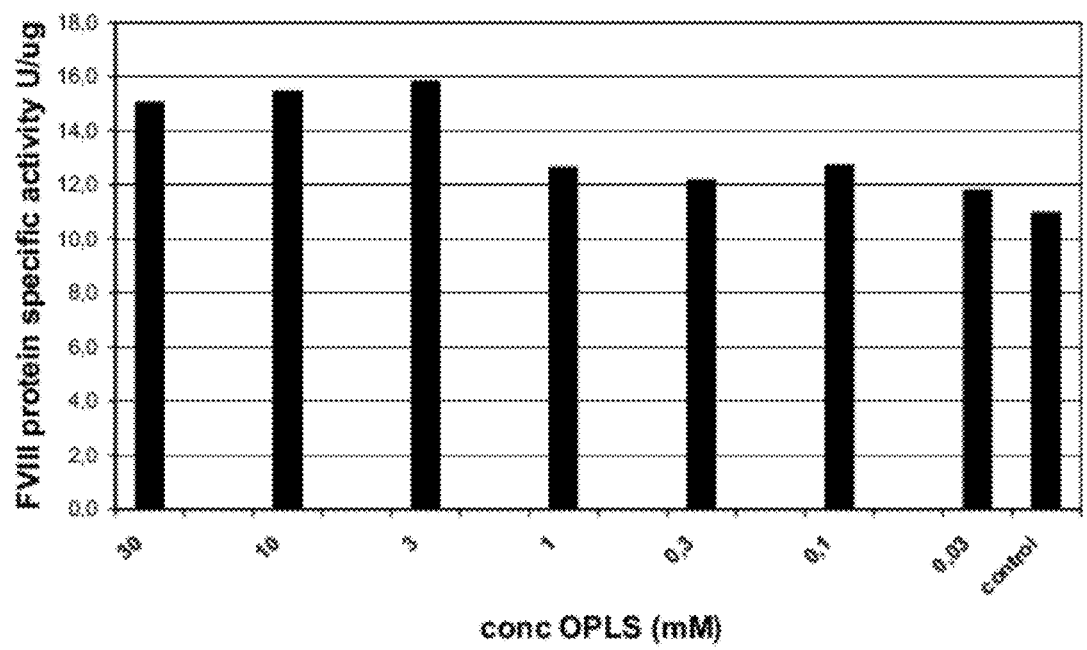

Conclusion:

Addition of OPLS increases the specific productivity of Factor VIII producing cells (see FIG. 2A) and addition of OPLS increases specific activity of Factor VIII (see FIG. 2B).

Example 2

Supplementing Serum-Free Cell Culture Medium of Factor VIII Producing Cells with O-phospho-L-serine and/or a Plant Hydrolysate BDD Factor VIII producing cells (1C5-SF cell line) were cultivated in 50 mL tubes with filter caps (Filter tubes 50 bioreactor, TPP). $2.5 \times 10^6$ cells in 5 mL CDM4CHO medium supplemented with O-phospho-L-serine to a concentration of 20 mM and/or a plant hydrolysate to a concentration of 5 mg/ml as shown in Table 4. Each condition was tested in four 5 mL cultures. The cultures were incubated in a shaking incubator (37° C., 8% $CO_2$ and 250 rpm). Four days after seeding, 1.2 mL of each culture was centrifuged 2000×g for 5 min, and the cell pellet was discarded. The supernatant was stabilized by addition of imidazol pH 7.2 to a final concentration of 20 mM and Tween 80 to a final concentration of 0.02% and frozen in aliquots of 0.2 mL at −80° C.

The total Factor VIII antigen content of each culture was determined by sandwich ELISA. Aliquots of stabilized and frozen medium were thawed and assayed as described in Materials and Methods. The content of Factor VIII recognized by the F25 antibody, which selectively binds Factor VIII with an intact heavy chain C-terminal, was determined. Aliquots of stabilized and frozen medium were thawed and assayed with the F25 ELISA as described in Materials and Methods.

For activity testing, aliquots of stabilized and frozen medium were thawed and assayed by CoA assay as described in Materials and Methods.

The quality of the Factor VIII in the medium of each culture was assessed with the specific activity calculated from the activity and the total Factor VIII antigen content. The proportion of the Factor VIII with intact heavy chain C-terminal was assessed from the relationship between the amount of Factor VIII antigen detected with the F25 ELISA and the total Factor VIII antigen amount.

Figure 3A:
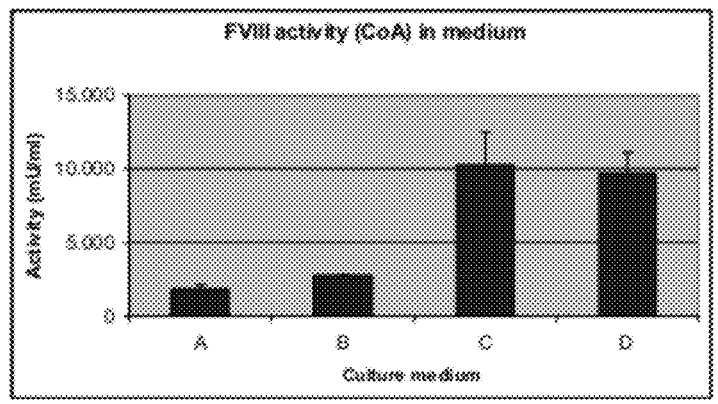
FIG. 3A-C. Effect of O-phospho-L-serine and/or a plant protein hydrolysate on Factor VIII in the medium of Factor VIII producing cells. The identity of the conditions A-D is shown in Table 4.
Figure 3B:
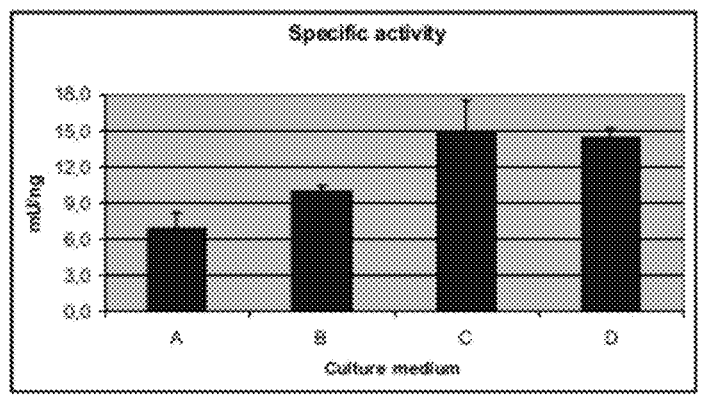
Figure 3C:
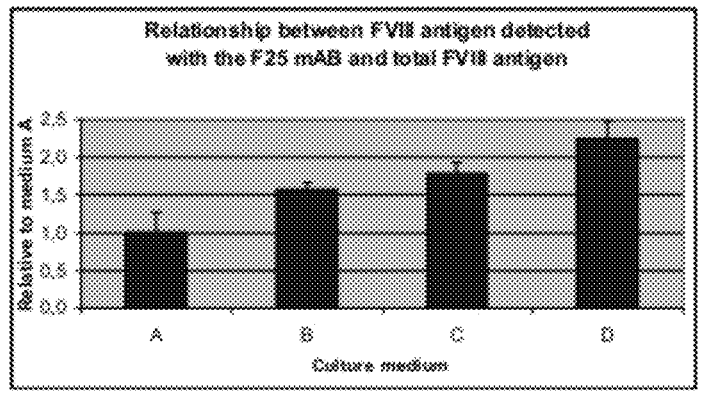

Results obtained with the two supplements are shown in FIG. 3A-C. These data demonstrate beneficial effects of adding either O-phospho-L-serine or a plant hydrolysate to the cultures of Factor VIII producing cells. Both supplements improved the yield and quality of recombinant Factor VIII from cell cultures, and both additives increased the proportion of Factor VIII with intact heavy chain C-terminal in the medium. Furthermore, an additive beneficial effect on the proportion of Factor VIII with intact heavy chain C-terminal were seen when O-phospho-L-serine and the plant hydrolysate were used in combination.

TABLE 4

| | Supplements tested with Factor VIII producing cells | | |
|---|---|---|---|
| | Product | Supplier | Catalog no. |
| A | No additive | — | — |
| B | Wheat gluten hydrolysate | Kerry Bioscience | HyPep 4605 |
| C | O-phospho-L-serine | Sigma | P0878 |
| D | Wheat gluten hydrolysate and O-phospho-L-serine | — | — |

The invention claimed is:

1. A method for the increased production of a Factor VIII polypeptide, the method comprising the steps of a) culturing a mammalian cell expressing a Factor VIII polypeptide in a cell culture medium free of animal-derived components comprising a C2-domain ligand, wherein the C2 domain ligand is O-Phospho-L-Serine (OPLS), and b) isolating the expressed Factor VIII polypeptide from the mammalian cell, to obtain a Factor VIII polypeptide, wherein the amount of Factor VIII polypeptide is increased relative to the amount of Factor VIII produced in the absence of OPLS.

2. A method for the increased production of a Factor VIII polypeptide, the method comprising the steps of a) culturing a mammalian cell expressing a Factor VIII polypeptide in a cell culture medium free of animal-derived components and b) isolating the expressed Factor VIII polypeptide from the mammalian cell, wherein the isolating comprises adding a C2-domain ligand, wherein the C2 domain ligand is OPLS, to the medium prior to removing the mammalian cells, to obtain a Factor VIII polypeptide, wherein the amount of Factor VIII polypeptide is increased relative to the amount of Factor VIII produced in the absence of OPLS.

3. The method according to claim 1, wherein the OPLS is present in the cell culture medium in a concentration of 0.1-100 mM.

4. The method according to claim 1, wherein the OPLS is added to the cells in step b) in a concentration of 1-200 mM.

5. The method according to claim 1, wherein the cell culture medium further comprises a soybean trypsin inhibitor.

6. The method according to claim 1, wherein the cell culture medium further comprises plant protein hydrolysate.

7. The method according to claim 1, wherein the mammalian cell is selected from the group consisting of mammalian cells that endogenously express the Factor VIII polypeptide and mammalian cells that have been transfected with a gene for the Factor VIII polypeptide.

8. The method according to claim 1, wherein the mammalian cell has been transfected with an expression vector comprising a nucleic acid molecule encoding the Factor VIII polypeptide and expression control regions operatively linked thereto.

9. The method according to claim 1, wherein the expressed Factor VIII polypeptide is harvested from the cell culture medium without substantially reducing the viability of the mammalian cells.

10. The method according to claim 9, wherein the production is continued using the same batch of mammalian cells.

11. The method according to claim 2, wherein the OPLS is present in the cell culture medium in a concentration of 0.1-100 mM.

12. The method according to claim 2, wherein the OPLS added to the mammalian cells in step b) is in a concentration of 1-200 mM.

13. The method according to claim 2, wherein the cell culture medium further comprises a soybean trypsin inhibitor.

14. The method according to claim 2, wherein the cell culture medium further comprises plant protein hydrolysate.

15. The method according to claim 2, wherein the mammalian cell is selected from the group consisting of mammalian cells that endogenously express the Factor VIII polypeptide and mammalian cells that have been transfected with a gene for the Factor VIII polypeptide.

16. The method according to claim 2, wherein the mammalian cell has been transfected with an expression vector comprising a nucleic acid molecule encoding the Factor VIII polypeptide and expression control regions operatively linked thereto.

17. The method according to claim 2, wherein the expressed Factor VIII polypeptide is harvested from the cell culture medium without substantially reducing the viability of the mammalian cells.

18. The method according to claim 17, wherein the production is continued using the same batch of mammalian cells.

19. The method of claim 1, further comprising c) purifying the Factor VIII polypeptide.

20. The method of claim 2, further comprising c) purifying the Factor VIII polypeptide.

21. The method of claim 1, wherein the amount of Factor VIII polypeptide is increased by at least 10% relative to the amount of Factor VIII produced in the absence of OPLS.

22. The method of claim 2, wherein the amount of Factor VIII polypeptide is increased by at least 10% relative to the amount of Factor VIII produced in the absence of OPLS.

* * * * *

SEQUENCE LISTING

<160> NUMBER OF SEQ ID NOS: 1

<210> SEQ ID NO 1
<211> LENGTH: 4416
<212> TYPE: DNA
<213> ORGANISM: Artificial Sequence
<220> FEATURE:
<223> OTHER INFORMATION: FVIII cDNA

<400> SEQUENCE: 1

```
atggaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggataggga     720 gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag aaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca aagttataa agtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat taagaatca agcaagcaga ccatataaca tctaccctca cggaatcact    1500
gatgtccgtc ctttgtattc aaggagatta ccaaaaggtg taaacatttt gaaggatttt    1560
ccaattctgc caggagaaat attcaaatat aaatggacag tgactgtaga agatgggcca    1620
```

```
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag agaaactgt cttcatgtcg     2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcgcgaca ccctagcact aggcaaaagc aatttaatgc cacccaccg     2340
gtcttgaaac gccatcaacg ggagatcact cgtactactc ttcagtctga tcaagaggaa    2400
attgactatg atgataccat atcagttgaa atgaagaagg aagattttga catttatgat    2460
gaggatgaaa atcagagccc ccgcagcttt caaaagaaaa cacgacacta ttttattgct    2520
gcagtgggaga ggctctggga ttatgggatg agtagctccc cacatgttct aagaaacagg   2580
gctcagagtg gcagtgtccc tcagttcaag aaagttgttt ccaggaatt tactgatggc    2640
tcctttactc agcccttata ccgtggagaa ctaaatgaac atttgggact cctggggcca    2700
tatataagag cagaagttga agataatatc atggtaactt tcagaaatca ggcctctcgt    2760
ccctattcct tctattctag cctttatttct tatgaggaag atcagaggca aggagcagaa   2820
cctagaaaaa actttgtcaa gcctaatgaa accaaaactt acttttggaa agtgcaacat    2880
catatggcac ccactaaaga tgagtttgac tgcaaagcct gggcttattt ctctgatgtt    2940
gacctggaaa aagatgtgca ctcaggcctg attggacccc ttctggtctg ccacactaac    3000
acactgaacc ctgctcatgg gagacaagtg acagtacagg aatttgctct gttttttcacc   3060
atctttgatg agaccaaaag ctggtacttc actgaaaata tggaaagaaa ctgcagggct    3120
ccctgcaata tccagatgga agatcccact tttaaagaga attatcgctt ccatgcaatc    3180
aatggctaca taatggatac actacctggc ttagtaatgg ctcaggatca aaggattcga    3240
tggtatctgc tcagcatggg cagcaatgaa acatccatt ctattcattt cagtggacat     3300
gtgttcactg tacgaaaaaa agaggagtat aaaatggcac tgtacaatct ctatccaggt    3360
gttttttgaga cagtggaaat gttaccatcc aaagctggaa tttggcgggt ggaatgcctt    3420
attggcgagc atctacatgc tgggatgagc acactttttc tggtgtacag caataagtgt    3480
cagactcccc tgggaatggc ttctggacac attagagatt tcagattac agcttcagga    3540
caatatggac agtgggcccc aaagctggcc agacttcatt attccggatc aatcaatgcc    3600
tggagcacca aggagcccct ttcttggatc aaggtggatc tgttggcacc aatgattatt    3660
cacggcatca agacccaggg tgcccgtcag aagttctcca gcctctacat ctctcagttt    3720
atcatcatgt atagtcttga tgggaagaag tggcagactc atcgaggaaa ttccactgga    3780
accttaatgg tcttctttgg caatgtggat tcatctggga taaaacacaa tatttttaac    3840
cctccaatta ttgctcgata catccgtttg cacccaactc attatagcat tcgcagcact    3900
cttcgcatgg agttgatggg ctgtgattta aatagttgca gcatgccatt gggaatggag    3960
```

```
agtaaagcaa tatcagatgc acagattact gcttcatcct actttaccaa tatgtttgcc    4020
acctggtctc cttcaaaagc tcgacttcac ctccaaggga ggagtaatgc ctggagacct    4080
caggtgaata atccaaaaga gtggctgcaa gtggacttcc agaagacaat gaaagtcaca    4140
ggagtaacta ctcagggagt aaaatctctg cttaccagca tgtatgtgaa ggagttcctc    4200
atctccagca gtcaagatgg ccatcagtgg actctctttt ttcagaatgg caaagtaaag    4260
gtttttcagg gaaatcaaga ctccttcaca cctgtggtga actctctaga cccaccgtta    4320
ctgactcgct accttcgaat tcaccccag agttgggtgc accagattgc cctgaggatg     4380
gaggttctgg gctgcgaggc acaggacctc tactga                              4416
```